United States Patent [19]
Richter et al.

[11] Patent Number: 5,622,708
[45] Date of Patent: Apr. 22, 1997

[54] ERODIBLE SANITIZING CAULK

[75] Inventors: Francis L. Richter, Circle Pines; Duane J. Reinhardt, Maplewood; Paula J. D. Carlson, Brooklyn Park, all of Minn.

[73] Assignee: Ecolab Inc., St. Paul, Minn.

[21] Appl. No.: 28,349

[22] Filed: Mar. 9, 1993

Related U.S. Application Data

[60] Continuation-in-part of Ser. No. 661,697, Feb. 27, 1991, abandoned, which is a division of Ser. No. 247,279, Sep. 21, 1988, Pat. No. 5,019,346.

[51] Int. Cl.$^6$ .................................................. A01N 25/02
[52] U.S. Cl. .................... 424/405; 424/409; 424/76.8
[58] Field of Search ............................. 424/405, 409, 424/76.8; 523/122, 216; 422/28, 29; 426/321, 323, 335

[56] References Cited

U.S. PATENT DOCUMENTS

| | | | |
|---|---|---|---|
| Re. 32,763 | 10/1988 | Fernholtz et al. | 252/90 |
| D. 280,757 | 9/1985 | Paulovich et al. | D23/3 |
| 2,087,592 | 7/1937 | Chesnut | 87/5 |
| 2,891,713 | 6/1959 | O'Neil | 229/51 |
| 3,112,499 | 12/1963 | Thornton | 4/222 |
| 3,597,772 | 8/1971 | Lincolnwood et al. | 4/222 |
| 3,721,629 | 3/1973 | Goodenough | 252/105 |
| 3,724,002 | 4/1973 | Buck, Jr. | 4/222 |
| 3,969,258 | 7/1976 | Carandang et al. | 252/106 |
| 4,218,432 | 8/1980 | Watanabe et al. | 424/14 |
| 4,224,701 | 9/1980 | Huang | 4/206 |
| 4,272,395 | 6/1981 | Wright | 252/106 |
| 4,318,193 | 3/1982 | Bayer et al. | 4/222 |
| 4,318,891 | 3/1982 | Kim | 422/263 |
| 4,536,367 | 8/1985 | Hung et al. | 422/37 |
| 4,571,410 | 2/1986 | Nevins et al. | 523/122 |
| 4,574,403 | 3/1986 | Dintemann et al. | 4/309 |
| 4,623,677 | 11/1986 | Nevins et al. | 523/122 |
| 4,624,713 | 11/1986 | Morganson et al. | 134/25.2 |
| 4,671,957 | 6/1987 | Holtshousen | 424/80 |
| 4,710,220 | 12/1987 | Pischky et al. | 71/67 |
| 4,738,728 | 4/1988 | Barford et al. | 134/34 |
| 4,820,449 | 4/1989 | Menke et al. | 252/544 |
| 4,837,008 | 6/1989 | Rudy et al. | 424/53 |
| 4,911,859 | 3/1990 | Bunczk et al. | 252/106 |
| 5,011,615 | 4/1991 | Minderman | 210/764 |
| 5,158,778 | 10/1992 | Donovan et al. | 424/488 |

FOREIGN PATENT DOCUMENTS

| | | |
|---|---|---|
| 0055023 | 11/1981 | European Pat. Off. . |
| 0227108 | 12/1986 | European Pat. Off. . |
| 0328335 | 8/1989 | European Pat. Off. . |
| 0460385 | 12/1991 | European Pat. Off. . |
| 1520238 | 5/1977 | Germany . |
| WO92/21238 | 12/1992 | WIPO . |

OTHER PUBLICATIONS

Technical Bulletin Shell Chemical Company, Bulletin No. SC:131–82.
FMC Technical Information.
Industrial Uses of ACL® Chlorinating Compositions, Monsanto Corp.

(List continued on next page.)

Primary Examiner—John C. Bleutge
Assistant Examiner—Robert H. Harrison
Attorney, Agent, or Firm—Merchant, Gould, Smith, Edell, Welter & Schmidt, P.A.

[57] ABSTRACT

The invention is an erodible antimicrobial caulk composition having a sanitizer and a hardener which controls the consistency and the dissolution rate of the composition once subjected to an aqueous flow. Also disclosed is a method of preparing the erodible caulk composition. These caulks are useful in institutional food preparation and food serving environments including restaurants, hospitals, day care facilities, nursing homes, and the like as well as institutional food harvesting and processing environments including food and beverage processing plants, dairy farms and dairy plant operations, red meat, poultry and fish preparation and processing environments, and the like, including post process food transport and distribution channel environments such as trucks and grocery or foodstuff retailers.

24 Claims, 2 Drawing Sheets

| | Penetration |
|---|---|
| CONTROL A | <20 millimeters |
| CONTROL B | <50 millimeters |
| EXAMPLE 36 | 343.0 millimeters |

OTHER PUBLICATIONS

Morton Thiokol, Inc. Material Safety Data Sheet.
Material Safety Data Sheet on Perox Red 32.
Union Carbide Material Safety Data Sheet, Mar. 11, 1981.
Cosmetic Ingredient Dictionary, Third Edition.
The Condensed Chemical Dictionary, Tenth Edition, Revised by Gessner G. Hawley.
Union Carbide Material Safety Data Sheet, Aug. 31, 1981.
Michael P. Doyle; Food Borne Pathogens of Recent Concern; Ann. Rev. Nut. 1985; vol. 5, pp. 25–41.
Official Methods of Analysis of the Association of Official Analytical Chemists, Fourteenth Edition, 1984.
Pesticide Assessment Guidelines, (U.S.) Environmental Protection Agency, Brochure No. PB83–153924.
Technical Information on BASF Wyandotte's PLURONIC Product Line.

GAF Chemicals Corp. Table II Physical Data oon Igepal CO Surfactants.

Articles, Blow Molding, Injection Molding, and Thermoforming, Wiley Encyclopedia of Packaging Technology, 54,406,668 (1986).

Germicidal Quaternaries, Group II—Cationics, Onyx Chemicals.

Physical Properties of Dowicide Products, Dow Chemical Co.

Technical Information on Shell's NEODOL Product Line.

Database WPI, Week 9304, Derwent Publications Ltd., London, GB; AN 032226, "Elastic Rubber Conditioned Sealing Antimicrobial Material", & JP,A,4 359 989 (Dainippon Printing) 14 Dec. 1992.

ERODIBLE SANITIZING CAULK

This application is a continuation-in-part of U.S. patent application Ser. No. 07/661,697 filed Feb. 27, 1991, abandoned, which is a division of U.S. patent application Ser. No. 247,279, filed Sept. 21, 1988 and now U.S. Pat. No. 5,019,346.

FIELD OF THE INVENTION

The invention generally relates to caulks, sealants, and grouts. More specifically, the invention relates to an erodible caulk composition containing an antimicrobial such as a quaternary ammonium salt which may be dispensed through manual application to surfaces or by extrusion from any appropriate dispenser.

BACKGROUND OF THE INVENTION

The troublesome reoccurrence of food born diseases caused by psychotropic, pathogenic micro-organisms has created strong concern within the food process industry and has fueled a search for new environmental sanitation products targeted at these micro-organisms. Public awareness of food born diseases has dramatically increased recently due to the occurrence of epidemics of both listeriosis and salmonellosis.

The symptoms of these diseases can manifest a number of different forms. In neonatal infants, the disease often can be characterized by symptoms of sepsis or meningitis. In pregnant women, the disease often takes the form of a puerperal sepsis or non-specific flu-like illness which can result in the premature delivery of stillborn or acutely ill infants. Doyle, M. P.; Food Borne Pathogens of Recent Concern; Ann. Rev. Nutr. 1985; Vol. 5, pages 25–41.

The FDA has responded to outbreaks of listeriosis and salmonellosis with expanded plant audits and new test protocols to isolate pathogens in those areas which foster microbiological contaminants. Pathogens present in the general plant environment will eventually find their way onto floors, into the drains as well as cracks and crevices and other small openings or voids where microbial growth may occur.

Previous attempts at preventing microbial growth include U.S. Pat. No. 3,597,772 to Leavitt et al which discloses a lavatory sanitation body comprising any nonionic, cationic, and amphoteric synthetic detergent in combination with an acidic agent.

EP Appln. No. 0,227,108 to Fukuchi et al discloses an oral composition generally comprising a toothpaste which includes carboxy methyl celluloses, anionic surfactants such as sodium lauryl sulfate, plasticizers such as propylene glycol, and alkyl amides. The alkyl amides are preferably alkylolamide fatty acid esters having 9–18 carbon atoms.

U.K. Patent No. 1,520,238 to Paulus et al discloses an antimicrobial caulk composition generally comprising an antimicrobial such as tetraethylthiuram disulfide and benzyl alcohol-hemiformal, hydroxy cellulose, polyphosphates, water and a pigment. The paste in major portion is comprised of hydroxy cellulose with the active antimicrobial being a combination of tetramethylenethiuram disulfide and benzyl alcohol hemiformals. In use, the composition is intended to be used in paints, paper material, and adhesives.

U.S. Pat. No. 4,571,410 to Nevins et al discloses a solvent base caulk comprising a solvent, an ethylene vinyl acetate copolymer mixture, a water white hydrocarbon resin such as an alpha-methylstyrene based resin, a thickening agent such as a glycol. Optionally, the composition may also comprise plasticizers, bactericides and antioxidants. Nevins et al disclose the use of a bactericide at 0.5–10 parts or antimicrobial such as Vinyzene from Morton Thiokol.

U.S. Pat. No. 4,671,957 to Holtshousen discloses an antibacterial cream generally comprising an antibacterial povidone-iodine constituent held in a hydrocarbon/polyol cream base. The cream may also comprise emulsifier such as a higher fatty acid or alcohol and may be used for topical applications such as burns on human or animal body skin.

EP Appln. No. 0,055,023 to Riffkin discloses an antiseptic adhesive composition generally comprising a rubbery elastomer such as a polyurethane or polyisobutylene, a water soluble or swellable hydrocolloids such as gelatin or pectin, and an antiseptic or germicidal agent such as an iodine, phenolic, and the like. Optionally, the Riffkin composition may also comprise a plasticizer, an antioxidant, or cohesive strengthening agent among other ingredients. The Riffkin composition is ultimately used to formulate adhesives for bandages for applications such as dermal ulcers and burn therapy.

U.S. Pat. No. 4,624,713 to Morganson et al discloses a solid rinse agent which generally comprises polyoxypropylene-polyoxyethylene block copolymer surfactants, urea, water, and various dispensing rate adjusting additives including carboxylic acids and alkanolamides for providing the desired rate of solubilization.

SUMMARY OF THE INVENTION

In accordance with a first aspect of the invention there is provided an erodible antimicrobial caulk composition comprising an antimicrobial and a hardener. Optionally, the erodible antimicrobial caulk composition may comprise, plasticizers such as alkyl glycols, solubility modifiers, organic and inorganic fillers, surfactants and detergents, solvents, acidulants and dyes as well as processing aids which will assist in formulation of the product, among other constituents.

In accordance with a further aspect of the invention there is also provided a method of using the various embodiments of caulk disclosed herein. In this context, the caulk is placed into various areas of use and, without need of equipment, dispensed through simple water contact in cleaning and rinsing operations. Once subjected to water contact, the caulk erodes dispensing the antimicrobial agent dispersed within the composition. The composition of the caulk may be altered to provide various levels of erosion, i.e., a controlled solubility or release mechanism for the antimicrobial agent. The caulk may either be dispensed from a tube through extrusion, "pressed in place" as a pre-extruded erodible rope, or otherwise manually applied as a paste or putty and inserted into position.

DETAILED DESCRIPTION OF THE PREFERRED EMBODIMENTS

Figure 1:
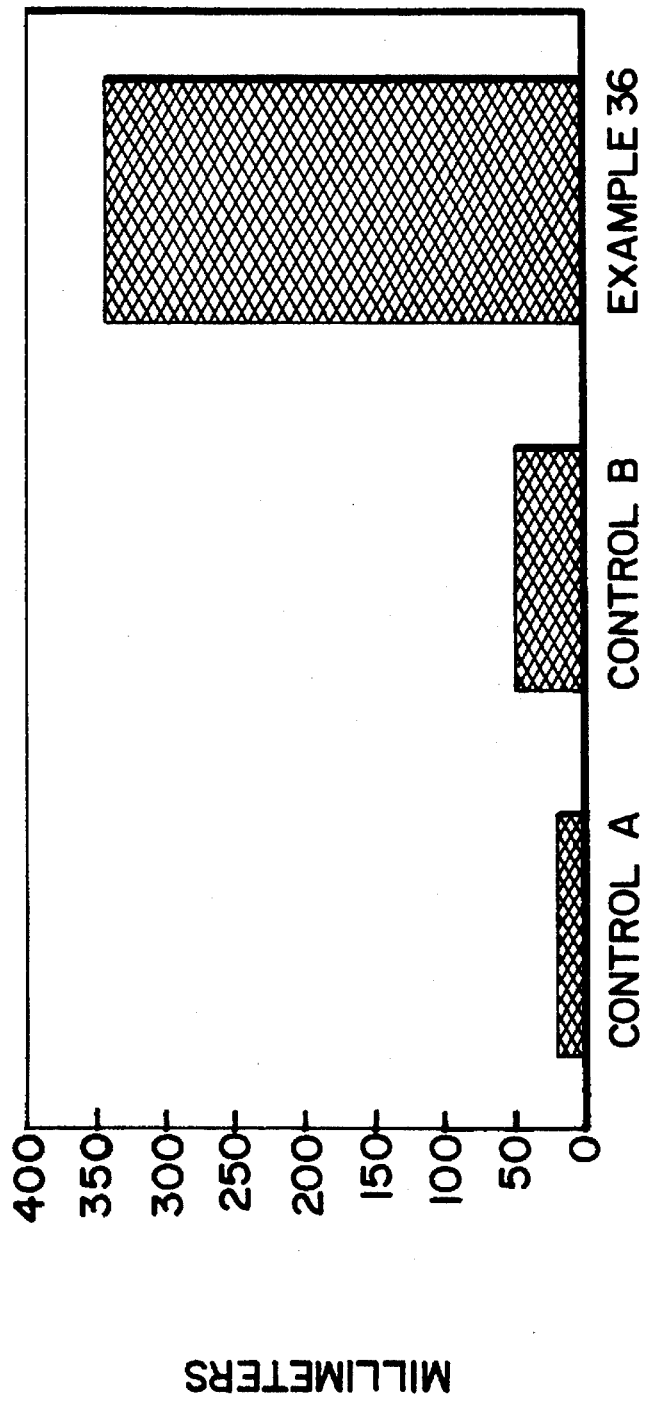
FIG. 1 is a graphical depiction of the results of a penetrometer analysis comparing one caulk embodiment of the invention against control compositions.

In the food processing industry, microbial growth is dependent on many factors including the foods processed, the processing environments, including the temperature of the food processing facility as well as the frequency with which the facility is cleaned. Ultimately, microbes are removed or destroyed through cleaning and sanitizing processes which rely on disposal or drainage. Consequently, any stagnant space within the food process facility, such as floor and wall cracks or crevices, presents an optimum host environment for the continued growth of microbes and bacterial contaminants which may lead to food born infectious diseases. By providing an active chemical cleaner which is capable of "sanitizing", the caulk of the invention precludes the growth of all but the most insignificant amount of microscopic contaminants.

Accordingly, the sanitizing agent used in the caulk of the invention preferably satisfies the definition of "sanitizer" as by the AOAC Official Methods of Analysis, Germicidal and Detergent Sanitizing Action §4.028 (1984). This AOAC use-dilution protocol is one of a small number of procedures generally recognized and professionally accepted for measuring biocidal activity.

The sanitizing agent used in the caulk of the invention should provide a "sanitizing" efficacy which will cause at least 3 log count reduction or 99.9% in the number of organisms within 30 seconds to enable use within food processing environments as required by EPA Guidelines for the food processing industry.

The disclosed chemical sanitizer is intended to ensure a continuous controlled release of the active sanitizing agents as well as detergents for the life of the caulk. Moreover, the caulk of the invention is intended to provide a certain degree of variability within its own chemical and physical properties. As a result, the caulk may be applied to any number of food processing environments while still providing effective sanitizing action on in place.

For example, the caulk of the invention is intended to have the same level of efficacy in a cold water, low flow drain environment as in a hot water, high flow drain environment with the variance of certain constituents and the chemical sanitizer. Constant sanitizing efficacy is provided by varying the concentration and solubility of the sanitizing agent of the invention.

The Caulk

The invention is an erodible sanitizing caulk composition comprising a sanitizer and a hardener which controls the consistency and the dissolution rate of the composition once subjected to an aqueous flow.

The sanitizing agent may be one or more agents which function to provide the microbicidal activity in the caulk. Specifically, the sanitizing agent used should preferably fall within the well defined category of "sanitizers" having the capability to provide the necessary reduction in bacteria. Moreover, the chosen sanitizing agent may also function to deodorize the undesirable odors which often accompany microbial growth. Biofilm build up tends to result from the growth of bacteria within the drain region or in crevices or cracks which line floor areas. Other soils such as milk soils and animal or vegetable processing by-products which also form in these regions, in turn, result in bacterial growth. The formation of this residue creates a harboring environment for the sustained growth of more bacteria. Accordingly, the chemical used as the sanitizing agent is intended to function as a detergent assisting in the cleaning and removal of biofilms and other soils in the general environment.

Generally, any solid or liquid chemical agent having a "sanitizing" level of bacteriocidal efficacy may be used as the sanitizing agent in the caulk. Chemical compositions known to impart sanitizing efficacy include aldehydes, carboxylic acids, peracids and peroxygen compounds, iodine and iodine complexes, interhalogens, phenolics, surface-active agents including acid-anionic, amphoteric and cationic surfactants, nitrogen compounds and polymers including alkylamines, and inorganic and organic halogen releasing agent such as chlorine, chlorine dioxide, bromine releasing agents and mixtures thereof.

Representative compositions which could be used as the sanitizing agent of the present invention are commonly available aldehydes such as formaldehyde and glutaraldehyde and respective condensate derivatives; alkylamines such as N-Dodecyl-1, 3-propane diamine and salts thereof; polymeric moieties such as polyhexamethylene biguianide available commercially as Vantocil™, Cosmocil™, and Baquacil™ sold by ICI Americas Inc. and ionene polymers such as WSCP sold by Buckman Laboratories, Inc.; saturated or unsaturated carboxylic acids such as $C_{8-14}$ fatty acids including octanoic acid, decanoic acid, dodecanoic acid, as well as dicarboxylic acids like sorbic acid, fatty acid mixtures, or fatty acid mixtures with other antimicrobial agents including hydrogen peroxide; iodophors such as iodine-nonionic surfactant complexes, iodine-polyvinyl pyrrolidone complexes, iodine-quaternary ammonium chloride complexes, and amphoteric iodine-amine oxide complexes and the like; interhalogen compounds such as iodine monochloride and iodine trichloride or their respective polyhalide anions; anionic surfactants such as dodecyl benzene sulfonic acid, sodium lauryl sulfate and sodium 1-octane sulfonate; amphoteric compounds such as the ampholyte dodecyldi-(aminethyl)-glycines marketed by Goldschmidt AG under the tradename Tego™, or the imidazole ring derivatives called Miranol™ by Miranol Chemical, Inc.; cationic surfactants such as the alkyl dimethyl benzyl ammonium chlorides and alkyl dimethyl ethyl benzyl ammonium chlorides or blends thereof distributed under the BTC™ trademark by Stepan Company or the Bardac®, Barquet® and Hyamine® series by Lonza, Inc.; cationic bisbiguanides such as the chlorhexidine salts; substituted phenolics such as o-phenylphenol, 2,4,5-trichlorophenol, P-tert-amylphenol o-benzy-p-chlorophenol commercially available from sources such as Dow Chemical company and Mobay Chemical Company; bis-phenols such as hexachlorophene and dichlorophene; organic chlorine releasing agents such as cyanurates, isocyanurates and cyanuric acids, which are commercially available from FMC and Monsanto as their CDB and ACL product lines, respectively; encapsulated or unencapsulated inorganic chlorine releasing agents such as alkalis and alkaline earth hypochlorites including NaOCl, KOCl, LiOCl, $Ca(OCl)_2$ and the like as well as chloramine and bromamine derivatives such as Chloroamine-T™ and Dichlora-mine-T™ manufactured by EM Laboratories, dichlorodimethyl hydantoin and bromochlorodimethyl hydantoin produced by BASF Corp. Wyandotte and Great Lakes respectively.

When a carboxylic acid sanitizer is used in the caulk of the invention, an acidulant may also be used to maintain the appropriate pH. Acidulants generally function to provide a pH in the caulk of the invention which allows for the reduction of antimicrobial growth. Carboxylic acids function more effectively to provide sanitizing efficacy, at a lower pH. Generally, for the carboxylic acids mentioned above, a pH ranging from about 1.5 to 4.5, preferably from about 2.0 to 3.5 and most preferably from about 2.5 to 3.0 is desirable. Further, acidulants generally found useful include organic and inorganic (mineral) acids such as citric acid, lactic acid, acetic acid, glycolic acid, adipic acid, tartaric acid, succinic acid, propionic acid, malic acid, alkane sulfonic acids, cycloalkane sulfonic acids, as well as phosphoric acid, nitric acid, hydrochloric acid, sulfuric acid, and the like or mixtures thereof.

The concentration of these acids may generally range from 2.0 wt-% to 20.0 wt-% depending upon the required pH's indicated above as well as the dilution of the acid.

Also found to be useful as the sanitizing agent within the caulk of the present invention are cationic surfactants including quaternary ammonium chloride surfactants such as n-alkyl($C_{12-18}$) dimethyl benzyl ammonium chloride, n-alkyl ($C_{14-18}$) dimethyl benzyl ammonium chloride, n-alkyl ($C_{12-14}$) ethyl benzyl ammonium chloride, n-alkyl ($C_{12-18}$) ethyl benzyl ammonium chloride, n-tetradecyl dimethyl benzyl ammonium chloride monohydrate, n-alkyl ($C_{12-14}$) dimethyl 1-naphthylmethyl ammonium chloride and dodecyl dimethyl ammonium chloride commercially available from manufacturers such as Stepan Company and Lonza Inc.

In one preferred mode, the sanitizing agent is a cationic quaternary alkyl dimethyl benzyl ammonium chloride having an alkyl chain length which generally can range from about $C_8$ to $C_{18}$. Quats have been found to be most preferable due to their commercial availability, easy incorporation into formulas and high sanitizing efficacy. These sanitizing agents are also preferred because of their compatibility to high water temperatures to the presence of high organic loads, stability and broad spectrum antimicrobial efficacy in variable high and low pH wash systems, inherent chemical deodorizing, and their non-staining, non-bleaching, non-corrosive nature. More preferably, the alkyl chain length of a quat will be from $C_{10}$ to about $C_{16}$ or mixtures thereof. Most preferably, the sanitizing agent used within the invention is a quaternary ammonium chloride conforming to the formula [$CH_3 (CH_2)_{13}N(CH_3)_2CH_2C_6H_5$]Cl— which in essence has a mixture of n-alkyl chain lengths including 60 wt-% $C_{14}$, 30 wt-% $C_{16}$, 5 wt-% $C_{12}$, and 5 wt-% $C_{18}$ and is commercially available from Stepan Co. as BTC™ 8249 and Lonza Inc. as BARQUAT™4280.

The concentration of the sanitizing agent within the caulk of the invention is dependent on a great number of factors including the intended environment of application, i.e., the volume of drain flowage over time, the temperature of the drain flowage, the hardness of the contact water, the sanitizing agent or agents used within the caulk, the physical volume of the caulk once in place and the concentration of the other constituents, such as the hardeners used in the caulk.

With these considerations in mind, the concentration of the sanitizing agent can vary broadly from about 2 wt-% to about 80 wt-% of the caulk. Given certain applications, the sanitizing agent may comprise a very small percentage of the formula if the intended performance requires a rapidly soluble sanitizing caulk. Conversely, the sanitizing agent may be utilized at extremely high percentages in caulks designed for very slow or controlled dissolving. Practicalities such as the physical characteristics of the caulk including the rate of hardening of the caulk of the invention most often dictate that the sanitizing agent be present in an intermediate concentration range from about 5 wt-% to 10 wt-% up to 60 wt-% of the caulk. Preferably, the sanitizing agent is present in a range of about 15 to 50 wt-% of the caulk which provides the greatest formulatory ease for varying the concentrations of hardeners within the formulation.

The caulk of the invention may also comprise a hardener. The primary functions of the hardener are to provide the desired malleability in the formed caulk and to control or modify the solubility of the sanitizing agent once mixed into the caulk and formed into an area of use. The nature of the caulk of the invention is such that more than one hardener may be used and, further, it is possible to optionally use a separate and distinct constituent to modify solubility.

The hardener used should be capable of forming a homogeneous matrix with the sanitizing agent when mixed. Only with a homogeneous mixture of hardener and sanitizing agent will the caulk be able to provide a uniform dissolution when exposed to drainage or other moisture. Moreover, given an intended use, the selected hardener by itself or in combination with an additional solubility modifying constituent should be able to promote varying degrees of aqueous solubility depending on the hardener chosen and the hardener concentration within the caulk.

Generally, any agent or combination of agents which provides the requisite degree of hardness and aqueous solubility may be used if compatible with the sanitizing agent. However, if the caulk is to be used in food process environments where there will be a high flow of heated drainage, the hardener should provide a relatively low degree of aqueous solubility. Such food processing environments are usually found in the critical filling and processing areas located within the food processing facilities.

In contrast, if the intended food processing environment has a lower flow or cool water drainage, the hardener should provide for a higher degree of aqueous solubility allowing release of an effective amount of the sanitizing agent from the caulk of the invention.

The hardener may be selected from any organic or inorganic compound which imparts a hardness and/or controls soluble character when placed in an aqueous environment. Compositions which can be used in the caulk of the invention to vary hardness and solubility include amides such as stearic monoethanolamide, lauric diethanolamide, and stearic diethanolamide available from Stepan Chemical as NINOL™ amides, and Scher Chemical Company as SCHERCOMID™ amide products.

Nonionic surfactants have also been found to impart varying degrees of hardness and solubility to the caulk of the invention. Often, to improve compatibility the nonionic surfactant may be combined with a coupler such as propylene glycol, hexylene glycol or polyethylene glycol commercially available from Union Carbide Corporation as CARBOWAX™.

Nonionics useful in this invention include alkyl phenol ethoxylates, dialkylphenol ethoxylates, alcohol ethoxylates, and ethylene oxide/propylene oxide block copolymers such as the PLURONIC™ surfactants commercially available from BASF Wyandotte, glycol esters, polyethylene glycol esters, sorbitan esters, polyoxyethylene sorbitan esters, sucrose esters, glycerol esters, polyglycerol esters, polyoxyethylene glycerol esters, polyethylene ethers. Nonionics particularly desirable as hardeners are those which are solid at room temperature and have an inherently reduced aqueous solubility.

Other compositions which may be used as hardeners within the caulk of the invention include urea also known as carbamide; modified starches or cellulosics which have been made water soluble through an acid or alkaline treatment processes including the acid processed amylose fraction of potato starch and various inorganics which impart solidifying properties to a heated liquid matrix upon cooling such as calcium carbonate, sodium sulfate and sodium bisulfate.

The hardener used in the invention can be any number of agents or combination of agents. However, for pre-extruded caulks which are manually pressed in place, amides and urea have been found to further the intended functions of the drain sanitizing article of the present invention. Specifically, alkanolamides provide formulation ease when combined with sanitizing agents, such as cationic surfactants, which allows for varied degrees of hardness and solubility and, in turn, versatile application to the many environments found in the food processing industry. Straight chain alkanoic acid amides provide a higher degree of insolubility with a corresponding higher degree of hardness.

Generally, the alkyl chain of these amides ranges from $C_{12}$ to about $C_{18}$. Alkanoic chains such as, for example, stearic chains, when part of an amide hardener produce a caulk wherein the sanitizing agent dissolves slowly as the hardener dissolves or disperses. Moreover, maintaining the amide as a monosubstituted amide, instead of a di-substituted amide, also ensures a high degree of insolubility and hardness.

In contrast, branched or di-substituted amides provide a higher degree of aqueous solubility with a lower degree of hardness and a resulting increase in chemical sanitizer solubility. It is thought that the degree of hardness in the resulting chemical sanitizer is related to the melting point of the amide constituent. Moreover, a di-substituted amide having an alkanoic chain of about $C_{12}$ to $C_{14}$ such as, for example a lauryl chain, defines a caulk having greater aqueous solubility and a much more malleable character. Hardeners such as lauric diethanolamide offer a contrasting extreme to hardeners such as a stearic monoethanolamide, and are more applicable to low flow, cold runoff drain environments.

Another hardener and solubility modifier found to be useful in the caulk of the invention is urea. The addition of urea to the caulk provides hardness without the usual decrease in aqueous solubility. As a result, urea can be used to provide a relatively high degree of aqueous solubility while maintaining a high degree of hardness. Such a caulk may be useful for areas which receive an inordinately low flow of drainage but yet have a persistently high degree of microbial load.

The quantity of hardener used varies depending upon the same considerations which affected the quantity or concentration of the sanitizing agent. In fact, if a solid sanitizing agent is used such as a cationic surfactant like a naphthalene substituted quaternary ammonium chloride such as dimethyl 1-naphthyl methyl ammonium chloride there may be no need at all to include a hardener.

However, a certain concentration of hardener is generally desirable within the caulk of the invention for purposes of altering the solubility of the caulk. Complimenting the broad general range of the sanitizing agent the hardener may be present at a level which varies from about 10 to about 70 wt-% of the caulk. Preferably, the hardener is present at a concentration of about 20 to 60 wt-% and most preferably a concentration of about 30 to 50 wt-% which provides the most versatility in the hardness and solubility of the caulk. One preferred hardener has been found to be a bis(alcohol ethoxylate) adipate comprising a dicarboxylic acid derivative formulated from adipic acid having either carboxyl end group esterified and capped with a $C_{18}$ ethoxylated alcohol. The resulting compound, a bis(alkyl alcohol ethoxylate) adipate, has the general formula:

$$[CH_3(CH_2)_x-(OCH_2CH_2)_y-OCH_2CH_2O-C(O)(CH_2)_2]_2$$

wherein x ranges from about 7 to 21, preferably about 15 to 19 and most preferably about 17 to 19, and y ranges from about 20 to 60, preferably about 30 to 50, and most preferably about 38 to 42.

Applicants have found that surfactants of this general formula are highly sensitive to shear stress allowing easy application of caulks formulated with these surfactants. Further, these surfactants have been found to provide caulks of the invention with a homogenous character and a stable viscosity over a broad temperature range. In one preferred embodiment, this nonionic surfactant is combined with dodecyl benzene sulfonic acid at a pH of about two or less. In another preferred embodiment of the caulk of the invention, this nonionic surfactant may be used with phosphoric acid at a pH of 3 or less and an acid-anionic sanitizer such as dodecyl benzene sulfonic acid or sulfonate, sodium lauryl sulfonate, sodium 1-octane sulfonate or mixtures thereof.

When used as a hardener, the surfactants of this general formula are used at a concentration level ranging from about 10 wt-% to 70 wt-%, preferably from about 20 wt-% to 60 wt-%, and most preferably from about 30 wt-% to 50 wt-%.

The composition of the invention may also comprise a plasticizer. Generally, the plasticizer's function within the caulk is to increase the caulk's workability, flexibility or dispensibility. Further, a plasticizer may be used to lower the melt viscosity, the second order transition temperature, or the elastic modulus of the caulk. Generally, the plasticizer may be melt mixed with the caulk or intermixed into the caulk through a common solvent with removal of the solvent by evaporation.

Generally, plasticizers affect the caulk through any number of mechanisms including increasing lubricity by decreasing intermolecular friction, decreasing the resistance to destruction of three dimensional crystals, and by increasing volume between polymeric constituents within the caulk allowing ease of movement between molecular constituents.

To this end, the plasticizer may comprise any organic or inorganic compound, monomeric moiety or polymeric composition suitable for these functions including water; short chain, long chain and cyclic saturated or unsaturated alcohols, aldehydes, carboxylic acids, and derivatives thereof; glycerols, polyglycerols, glycols and polyglycols, including copolymers, ethers and esters thereof; ethoxylated and alkoxylated amines; phosphate esters; any number of petroleum hydrocarbons and hydrocarbon mixtures or derivatives such as mineral oils, petrolatums, and paraffin waxes; any number of refined natural oils derived from vegetable or animal origin and their reaction derivatives; or mixtures thereof.

When in use, plasticizers may be present in the system at a concentration ranging from about 0 wt-% to 50 wt-%, preferably about 5 wt-% to 40 wt-%, and most preferably about 10 wt-% to 30 wt-%. The inclusion of a greater concentration of plasticizer will tend to affect the physical properties of the caulk of the invention. Specifically, a greater concentration of plasticizer may tend to lower the melting point of the caulk while at the same time making the caulk more susceptible to dissolution through heated flow. In contrast, the omission of a plasticizer or the minimalization of plasticizer concentration may result in a caulk which is not easily formed into place or susceptible to dispensing through standard dispenser mechanisms such as applicator tubes and the like.

Caulk Formulation

Depending upon the given environment of application for the caulk, the caulk may comprise any assortment of ingredients including antimicrobials, hardeners, fillers plasticizers, acidulants, dyes, and the like. For example, if the caulk of the invention comprises one or more antimicrobials and a hardener, the caulk may generally be formulated by heat melting the constituents together at a temperature which will not destabilize the antimicrobial generally ranging from about 125° F. to 225° F., preferably from about 135° F. to 215° F., and most preferably about 145° F. to 205° F. depending upon the antimicrobial system of the composition.

Once the formulation has been adequately heated and the ingredients melted and blended together, the composition is allowed to cool. In order to produce the desired malleability or softness in the caulk, the caulk may be additionally kneaded or extruded to provide a penetrometer rating ranging from about 150 mm to 400 mm, preferably about 250 mm to 400 mm, and most preferably about 325 mm to 375 mm. The penetrometer rating may be obtained through any number of pressing, kneading, extrusion or other processes known to those of skill in the art. One method known to those of skill in the art is ASTM method D217-60T as provided for in Example 42 herein.

Such processing is especially relevant where the composition comprises a urea hardener. While not wishing to be bound by any given theory, Applicants believe that urea sets up an extended crystalline structure which is formed through mixing and extended heating. Upon cooling, the crystalline structure forms and solidifies. By pressing, kneading or extrusion, the crystalline structure is broken down by physical action which affects modulation of plasticity.

If a caulk is desired which can be dispensed from a caulk tube or other dispenser known to those of skill in the art, the composition may additionally comprise a constituent which modulates plasticity chemically. We have found that a solid having a given penetrometer hardness provides the following physical characteristics:

| Hardness | Relative Consistency |
|---|---|
| <50 mm | Very Hard Solid |
| 50–150 mm | Hard Solid |
| 150–250 mm | Soft Solid |
| 250–400 mm | Very Soft Solid |

In order to provide a caulk which may be easily pressed in place a penetrometer rating of 150 mm is preferred. In order to provide a caulk which may be extruded from a tube, a penetrometer rating of at least 250 mm is preferred.

WORKING EXAMPLES

Applicant now provides working examples which are intended to illustrate the various aspects, features, and advantages of the invention. However, these examples should not be construed as, in any way, limiting of the invention.

EXAMPLES 1 THROUGH 36

The erodible caulk composition of the invention (Examples 1–36), was mixed by charging the sanitizer into a mixing tank and heating with appropriate agitation. This controlled agitation prevents the entrapment of air and, in turn, excessive foam in the mix. The hardener and optionally the plasticizer are then slowly metered into the sanitizing agent with continued agitation. The mixture is then heated and agitated until a hardening constituent is melted or dissolved. Once dissolved, the caulk compositions were then decanted into individual containers.

| CONSTITUENT (Wt-%) | 1 | 2 | 3 |
|---|---|---|---|
| Alkyl Dimethyl Benzyl Ammonium Chloride | 42.00 | 42.00 | 42.00 |
| Stearic Diethanolamide | 24.00 | 23.99 | 23.99 |
| Stearic Monoethanolamide | 12.00 | 12.00 | 12.00 |
| PROPYLENE GLYCOL (USP) | | | 21.50 |
| UREA | 22.00 | 21.50 | |
| Morton FL Yellow G | | 0.01 | 0.01 |
| MAZU DF-210 SX (dimethylsiloxane) | | 0.50 | 0.50 |

| CONSTITUENT (Wt-%) | 4 | 5 | 6 |
|---|---|---|---|
| Alkyl Dimethyl Benzyl Ammonium Chloride | 42.00 | 42.00 | 42.00 |
| Stearic Diethanolamide | 23.99 | 24.49 | 24.49 |
| Stearic Monoethanolamide | 12.00 | 12.00 | 8.50 |
| PROPYLENE GLYCOL USP | 10.75 | 21.50 | 25.00 |
| Morton FL Yellow G | 0.01 | 0.01 | 0.01 |
| MAZU DF-210 SX (dimethylsiloxane) | 0.50 | | |
| Isopropanol (91% w/v) | 10.75 | | |

| CONSTITUENT (Wt-%) | 7 | 8 | 9 |
|---|---|---|---|
| Alkyl Dimethyl Benzyl Ammonium Chloride | 42.00 | 42.00 | 42.00 |
| Stearic Diethanolamide | 27.99 | 31.99 | 32.00 |
| Stearic Monoethanolamide | 8.00 | 4.00 | |
| PROPYLENE GLYCOL USP | 22.00 | 22.00 | 26.00 |
| Morton FL Yellow G | 0.01 | 0.01 | |

| CONSTITUENT (Wt-%) | 10 | 11 | 12 |
|---|---|---|---|
| Alkyl Dimethyl Benzyl Ammonium Chloride | 42.00 | 42.00 | 39.00 |
| Stearic Diethanolamide | 28.00 | 30.00 | 31.98 |
| Stearic Monoethanolamide | 4.00 | 2.00 | |
| PROPYLENE GLYCOL USP | 26.00 | 26.00 | 26.00 |
| Morton Blue E | | | 0.02 |
| Dextrin (yellow) | | | 3.00 |

| CONSTITUENT (Wt-%) | 13 | 14 | 15 |
|---|---|---|---|
| Alkyl Dimethyl Benzyl Ammonium Chloride | 36.00 | 25.00 | 37.00 |
| Stearic Diethanolamide | 31.98 | 31.98 | 27.99 |
| Stearic Monoethanolamide | | | 8.00 |
| PROPYLENE GLYCOL USP | 26.00 | 26.00 | 22.00 |
| Morton FL Yellow G | 0.015 | 0.01 | 0.01 |
| Morton Blue E | 0.005 | 0.01 | |
| Dextrin (yellow) | 6.00 | 17.00 | |
| Bentonite, refined montmorillonite clay | | | 5.00 |

| CONSTITUENT (Wt-%) | 16 | 17 | 18 |
|---|---|---|---|
| Alkyl Dimethyl Benzyl Ammonium Chloride | 39.00 | 36.00 | 42.00 |
| Stearic Diethanolamide | 28.00 | 28.00 | 32.98 |
| Stearic Monoethanolamide | 8.00 | 8.00 | |
| PROPYLENE GLYCOL (USP) | 22.00 | 22.00 | 22.00 |
| Morton FL Yellow G | | | 0.02 |
| Fumed Silica | 3.00 | 6.00 | |
| Silica | | | 3.00 |

| CONSTITUENT (Wt-%) | 19 | 20 | 21 |
|---|---|---|---|
| Alkyl Dimethyl Benzyl Ammonium Chloride | 42.00 | 39.00 | 42.00 |
| Stearic Diethanolamide | 29.98 | 32.98 | 24.50 |
| Stearic Monoethanolamide | | | 12.00 |
| PROPYLENE GLYCOL (USP) | 22.00 | 25.00 | |
| Morton Blue E | 0.02 | 0.02 | |
| Silica | 6.00 | 3.00 | |
| Ethanol | | | 21.50 |

| CONSTITUENT (Wt-%) | 22 | 23 | 24 |
|---|---|---|---|
| Alkyl Dimethyl Benzyl Ammonium Chloride | 42.00 | 42.00 | 42.00 |
| Stearic Diethanolamide | 24.50 | 24.50 | 24.50 |
| Stearic Monoethanolamide | 12.00 | 12.00 | 12.00 |
| Silica | 10.75 | | |
| Ethanol | 10.75 | 21.50 | |
| Mineral Oil | | | 21.50 |

| CONSTITUENT (Wt-%) | 25 | 26 | 27 |
|---|---|---|---|
| Alkyl Dimethyl Benzyl Ammonium Chloride | 35.00 | 42.00 | 35.00 |
| Stearic Diethanolamide | 31.50 | 24.50 | 31.50 |
| Stearic Monoethanolamide | 12.00 | 12.00 | 12.00 |
| Ethanol | 21.50 | | |
| Mineral Oil | | | 21.50 |
| Polyethylene Glycol (mw 4000) | | 21.50 | |

| CONSTITUENT (Wt-%) | 28 | 29 | 30 |
|---|---|---|---|
| Alkyl Dimethyl Benzyl Ammonium Chloride | 35.00 | 30.00 | 25.00 |
| Stearic Diethanolamide | 24.50 | 24.50 | 24.50 |
| Stearic Monoethanolamide | 12.00 | 12.00 | 12.00 |
| Mineral Oil | 28.50 | 33.50 | 38.50 |

| CONSTITUENT (Wt-%) | 31 | 32 | 33 |
|---|---|---|---|
| Alkyl Dimethyl Benzyl Ammonium Chloride | 20.00 | 10.00 | 10.00 |
| Stearic Diethanolamide | 24.50 | 24.50 | 24.50 |
| Stearic Monoethanolamide | 17.00 | 17.00 | 17.00 |
| Mineral Oil | 38.50 | 48.50 | 38.50 |
| PETROLATUM | | | 10.00 |

| CONSTITUENT (Wt-%) | 34 | 35 | 36 |
|---|---|---|---|
| Alkyl Dimethyl Benzyl Ammonium Chloride | 20.00 | 20.00 | 20.00 |
| Stearic Diethanolamide | 24.50 | 24.50 | 24.50 |
| Stearic Monoethanolamide | 14.50 | 15.50 | 15.50 |
| Morton FL Yellow G | | | 0.02 |
| Mineral Oil | 41.00 | 40.00 | 39.98 |

WORKING EXAMPLES 37–39

A study was conducted to measure antimicrobial levels present in use dilutions of erodible sanitizing caulk during dispensing at various water temperatures.

An analysis of antimicrobial concentration at differing water flow temperatures was undertaken using the formulation of Working Example 36. The conditions for each analysis are provided along with results.

EXAMPLE 37

70° F. Water, 25–30 psi, 9" cylinder

| Wt. | Wt. Loss in gms. | % Loss | Time (Minutes) |
|---|---|---|---|
| 67.24 | — | — | 0 |
| 63.75 | 3.49 | 5.19 | 5 |
| 59.60 | 4.15 | 11.36 | 10 |
| 57.53 | 2.07 | 14.44 | 15 |
| 54.34 | 3.19 | 19.19 | 20 |
| 49.96 | 4.38 | 25.70 | 25 |
| 46.17 | 3.79 | 31.34 | 30 |
| 42.75 | 3.42 | 36.42 | 35 |
| 40.32 | 2.43 | 40.04 | 40 |
| 37.80 | 2.52 | 43.78 | 45 |
| 35.11 | 2.69 | 47.78 | 50 |
| 32.35 | 2.76 | 51.89 | 55 |
| 30.19 | 2.16 | 55.10 | 60 |

Based on the results provided above, 37.05 gm caulk product were dispensed in 60 min. which equals 6.669 gm active antimicrobial quat based on 90% active alkyl dimethyl benzyl ammonium chloride in the formula at 20%. 6.669 gm alkyl dimethyl benzyl ammonium chloride in 9564 gm water based on 159.4 gm/min. equals 696.8 ppm active alkyl dimethyl benzyl ammonium chloride in the use dilution.

EXAMPLE 38

95° F. water, 25–30 psi, 9" cylinder

| Wt. | Wt. Loss in gms. | % Loss | Time (Minutes) |
|---|---|---|---|
| 68.68 | — | — | |
| 54.89 | 13.79 | 20.08 | 5 |
| 43.07 | 11.82 | 37.29 | 10 |
| 31.67 | 11.40 | 53.89 | 15 |
| 21.40 | 10.27 | 68.84 | 20 |
| 15.13 | 6.27 | 77.97 | 25 |
| 8.52 | 6.61 | 87.59 | 30 |
| 4.44 | 4.08 | 93.54 | 35 |
| 2.22 | 2.22 | 96.77 | 40 |
| 1.05 | 1.17 | 98.47 | 45 |
| 0.18 | 0.87 | 99.74 | 50 |

Based on the results above, 68.5 gm caulk product were dispensed in 50 min. which equals 12.33 gm active antimicrobial based on 90% active alkyl dimethyl benzyl ammonium chloride in the formula at 20%. 12.33 gm alkyl dimethyl benzyl ammonium chloride in 7970 gm water based on 159.4 gm/min. equals 1544.6 ppm active alkyl dimethyl benzyl ammonium chloride in the use dilution.

EXAMPLE 39

120° F. water, 25–30 psi, 9" cylinder

| Wt. | Wt. Loss in gms. | % Loss | Time (Minutes) |
|---|---|---|---|
| 61.14 | — | — | 0 |
| 37.80 | 23.34 | 38.17 | 5 |
| 15.50 | 22.30 | 74.65 | 10 |
| 1.32 | 14.18 | 97.84 | 15 |

Based on the results above, 59.82 gm caulk product were dispensed in 15 min. which equals 59.82 gm active antimicrobial based on 90% active alkyl dimethyl benzyl ammonium chloride in the formula at 20%. 59.82 gm alkyl dimethyl benzyl ammonium chloride in 2391 gm water based on 159.4 gm/min. equals 4483.3 ppm active alkyl dimethyl benzyl ammonium chloride in the use dilution.

EXAMPLE 40

A non-food contact sanitizing test was performed on Example 36 against E. aerogenous with a 5 minute contact time. Test was performed in the presence of a 5% serum and 5% milk organic soil load. Product was prepared at a concentration of 120 ppm active quat in 500 ppm hard $H_2O$. Results are as follows:

| Log Reduction of Colony Forming Units | |
|---|---|
| 5% Serum | 5% Milk |
| >3.0 | >3.0 |

Example 36 with both organic soil loads achieved >3.0 log reduction against *E. aerogenous* which is the required standard for non-food contact sanitizing.

EXAMPLE 41

A second non-food contact sanitizing test was performed on Example 36 against *S. aureus* with a 5 minute contact time. The test was performed in the presence of an organic soil represented by 5% serum and 5% milk. The product was prepared at a concentration of 120 pm active quat in 500 ppm hard $H_2O$. Results are as follows:

| Log Reduction of Colony Forming Units | |
|---|---|
| 5% Serum | 5% Milk |
| >3.0 | >3.0 |

Example 36 with both organic soil load achieved >3.0 log reduction against *S. aureus*, the required standard for non-food contact sanitizing.

EXAMPLE 42

A penetrometer analysis was undertaken on the formulation of Example 36. The control formulations comprised:

| Constituent | Control A | Control B |
|---|---|---|
| Alkyl Dimethyl Benzyl Ammonium Chloride | 55.00 | 42.00 |
| Propylene Glycol | 5.00 | 5.00 |
| Stearic Diethanolamide | | 21.91 |
| Stearic Monoethanolamide | 39.98 | 10.97 |
| Urea | | 19.65 |
| Morton Perox Red 32 | 0.02 | |
| Morton Blue E | | 0.02 |
| MAZU DF-210 SX (dimethylsiloxane) | | 0.45 |

Penetrometer results can be seen in FIG. 1 from using an evaluation at 70° F. over 30 seconds using a modification of ASTM standard method D217-60T, Cone Penetration of Lubricating Grease. A Precision Penetrometer Model 73510 was refitted with a Precision Needle #73520 (in place of standard cone), designed for evaluation of hard and semi-solids. Penetration time was increased from 5 to 30 seconds.

EXAMPLE 43–69

Using the same formulatory method as before (Examples 1–36), Examples 43–69 were then formulated with constituents as follows:

| Constituent (Wt-%) | 43 | 44 | 45 |
|---|---|---|---|
| $H_2O$ | 15.00 | 30.00 | 24.00 |
| Pluronic F-108 (Polyoxyethylene 256M) Polyoxypropylene (54M)) | 40.00 | 35.00 | 28.00 |
| Ethanol | 25.00 | 15.00 | 12.00 |
| Octanoic Acid | 10.00 | 10.00 | 8.00 |
| Phosphonic Acid (75% w/v) | 10.00 | 10.00 | 8.00 |
| Decanoic Acid | | | 12.00 |
| Dodecanoic Acid | | | 8.00 |

| Constituent (Wt-%) | 46 | 47 | 48 |
|---|---|---|---|
| $H_2O$ | 35.00 | 90.00 | 20.00 |
| Alkyl Dimethyl Benzyl Ammonium Chloride | | | 20.00 |
| Pluronic F-108 (Polyoxyethylene 256M) Polyoxypropylene (54M) | 30.00 | | |
| Ethanol | 15.00 | | |
| Octanoic Acid | 10.00 | | |
| Phosphonic Acid (75% w/v) | 10.00 | | |
| Stearic Diethanolamide | | 10.00 | |
| Bis(alcohol C-18 ethoxylate$_{40}$) adipate | | | 60 |

| Constituent (Wt-%) | 49 | 50 | 51 |
|---|---|---|---|
| $H_2O$ | 10.00 | 30.00 | |
| Alkyl ($C_{12}$) Dimethyl Benzyl Ammonium Chloride (ECOLAB) | 20.00 | 20.00 | |
| Alkyl ($C_{14}$) Dimethyl Benzyl Ammonium Chloride (Stepan) | | | 20.00 |
| Bis(alcohol C18 ethoxylate$_{40}$) adipate | 70.00 | 50.00 | 70.00 |
| Propylene Glycol | | | 10.00 |

| Constituent (Wt-%) | 52 | 53 | 54 | 55 |
|---|---|---|---|---|
| $H_2O$ | | 85.00 | 75.00 | 50.00 |
| Alkyl ($C_{12}$) Dimethyl Benzyl Ammonium Chloride (ECOLAB) | | 5.00 | 5.00 | 5.00 |
| Alkyl ($C_{14}$) Dimethyl Benzyl Ammonium Chloride (Stepan) | 20.00 | | | 20.00 |
| Bis(alcohol C18 ethoxylate$_{40}$) adipate | 60.00 | 10.00 | 10.00 | |
| Polyethylene Glycol (mw 8000) | | | 10.00 | 25.00 |
| Propylene Glycol | 20.00 | | | |

| Constituent (Wt-%) | 56 | 57 | 58 |
|---|---|---|---|
| $H_2O$ | 50.00 | 82.00 | 80.00 |
| Alkyl Dimethyl Benzyl Ammonium Chloride | 5.00 | 5.00 | 5.00 |
| Bis(alcohol C18 ethoxylate$_{40}$) adipate | 20.00 | 10.00 | 10.00 |
| Polyethylene Glycol (MW 400) | | | 5.00 |
| Propylene Glycol | 25.00 | | |
| White Mineral Oil | | 3.00 | |

| Constituent (Wt-%) | 59 | 60 | 61 |
|---|---|---|---|
| $H_2O$ | 82.00 | 85.00 | 80.00 |
| Alkyl Dimethyl Benzyl Ammonium Chloride | 5.00 | | 10.00 |
| Bis(alcohol C18 ethoxylate$_{40}$) adipate | 10.00 | 10.00 | 10.00 |

| | | | |
|---|---|---|---|
| Alfol 1012 Alcohol | 3.00 | | |
| Dodecyl Benzene Sulfonic Acid (97% w/v) | 5.00 | | |

| Constituent (Wt-%) | 62 | 63 | 64 |
|---|---|---|---|
| H$_2$O | 65 | 75.55 | 75.00 |
| Alkyl Dimethyl Benzyl Ammonium Chloride | | | 15.00 |
| Bis(alcohol C18 ethoxylate$_{40}$ adipate | 30 | 20 | 10.00 |
| Sulfonic Acid (97% w/v) | 5 | 4.45 | |

| Constituent (Wt-%) | 65 | 66 | |
|---|---|---|---|
| H$_2$O | 62.00 | 50.00 | |
| Bis(alcohol C18 ethoxylate$_{40}$) adipate | | 47.00 | |
| Polyethylene Glycol Distearate | 35.00 | | |
| Dodecyl Benzene Sulfonic Acid (97% w/v) | 3.00 | 3.00 | |

| Constituent (Wt-%) | 67 | 68 | 69 |
|---|---|---|---|
| H$_2$O | 25.00 | 47.00 | 44.00 |
| Bis(alcohol C18 ethoxylate$_{40}$) adipate | 47.00 | 47.00 | 47.00 |
| Propylene Glycol | 25.00 | 3.00 | 6.00 |
| Dodecyl Benzene Sulfonic Acid (97% w/v) | 3.00 | 3.00 | 3.00 |

EXAMPLE 70

Figure 2:
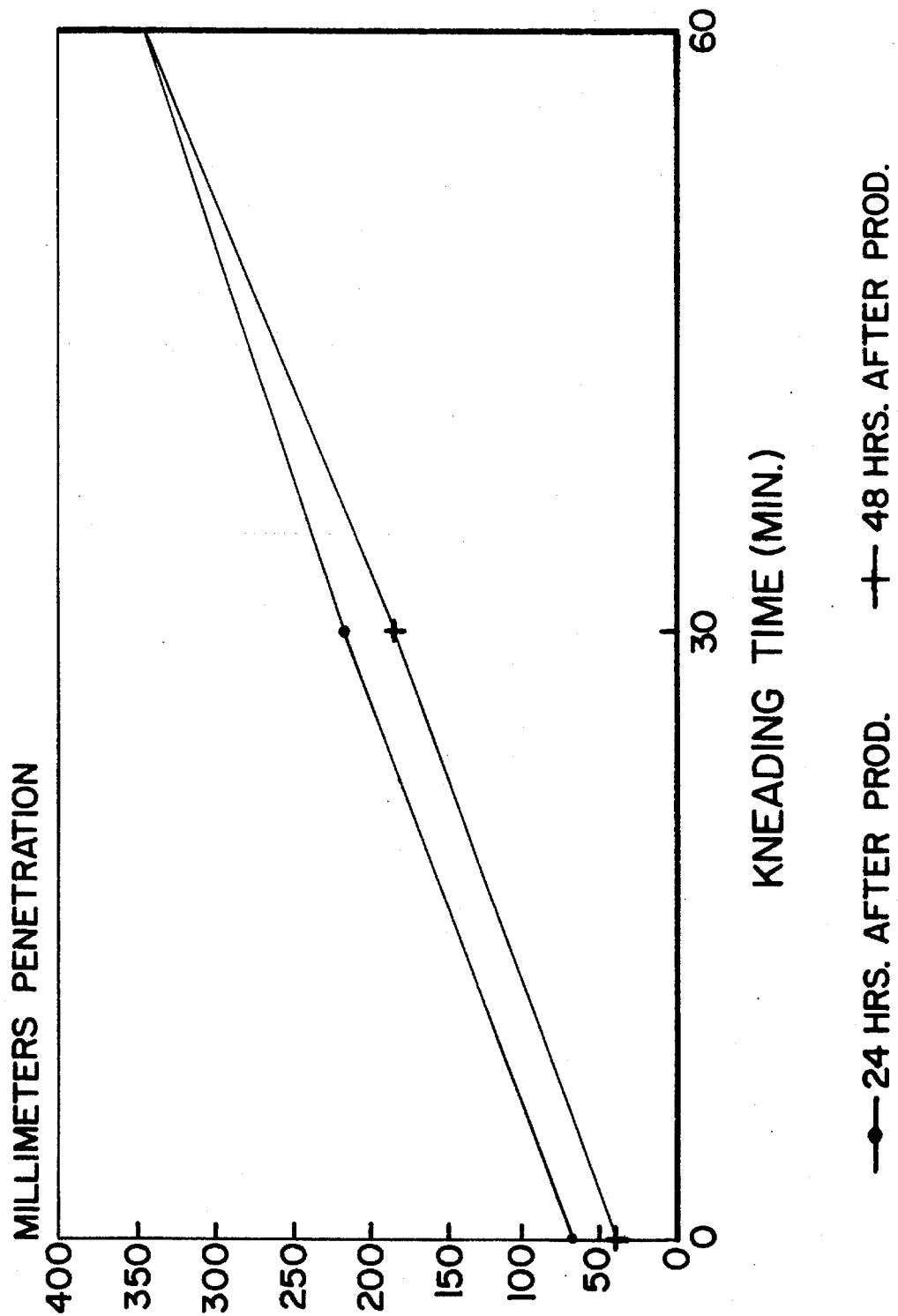
FIG. 2 is a graphical depiction of the results of the penetrometer analysis of Working Example 70.

An experiment was then undertaken to determine whether a caulk hardened with urea could be softened by kneading. Control B of Example 42 was evaluated by kneading with a Hobart model N-50 blender (similar to typical home cake/dough mixer). After the Control B formulation was made by hot melt/pour method and split, it was allowed to cool to room temperature and harden. Half was kneaded after 24 hours; half after 48 hours. The purpose of the first cooling was to allow urea crystals to develop before fracturing through the kneading process. The results of the analysis can be seen in FIG. 2.

The above discussion, examples, and data illustrate our current understanding of the invention. However, since many variations of the invention can be made without departing from the spirit and scope of this invention, the invention resides wholly in the claims hereinafter appended.

We claim as our invention:

1. An erodible sanitizing caulk composition which controllably solubilizes when contacted with water to provide a solution with sanitizing antimicrobial efficacy, said composition further comprising:
    (a) from about 5 wt-% to 60 wt-% of sanitizer, said sanitizer selected from the group consisting of an aldehyde compound, a carboxylic acid, a peracid compound, a peroxygen compound, an idophor complex, an interhalogen, a phenolic compound, a surface active agent, a quaternary ammonium salt, halogen releasing agent, and mixtures thereof; and
    (b) from about 10 wt-% to 70 wt-% of hardener wherein said hardener controls the consistency of said caulk and the dissolution rate of caulk once subjected to an aqueous flow and said caulk has penetrometer softness ranging from about 150 mm to 400 mm, said caulk solubilizing at a rate to provide a solution having at least about 120 parts per million sanitizer when contacted with water.

2. The composition of claim 1 wherein said sanitizer is selected from the group consisting of an aldehyde compound, an iodophor complex, a carboxylic acid, a quaternary ammonium salt, a peracid compound, an interhalogen, a phenolic compound, a surface active agent, a halogen releasing agent and mixtures thereof.

3. The composition of claim 1 wherein said hardener is selected from the group consisting of an amide compound, a nonionic surfactant, a starch compound, an inorganic salt, and mixtures thereof.

4. The composition of claim 1 additionally comprising from about 5 wt-% to 50 wt-% of a plasticizer.

5. The composition of claim 4 wherein said plasticizer is selected from the group consisting of water, an alkyl alcohol, an alkoxylated aldehyde compound, a carboxylic acid, a polyol, an amine compound, a phosphate ester, a petroleum based hydrocarbon, a vegetable oil, and mixtures thereof.

6. The composition of claim 1 wherein said hardener comprises a bis(alkyl alcohol ethoxylate) adipate having from about 20 to 60 moles of ethoxylation.

7. The composition of claim 2 wherein said sanitizer comprises an acid anionic surfactant selected from the group consisting of dodecyl benzene sulfonic acid, sodium lauryl sulfate, sodium 1-octane sulfonate, and mixtures thereof.

8. The composition of claim 1 wherein when subjected to an aqueous flow of about 70° F. or greater said caulk dissolves at a rate of about 5 wt-% or greater every five minutes.

9. The composition of claim 1 wherein said caulk has a penetrometer softness ranging from about 250 mm to 400 mm.

10. An erodible sanitizing caulk composition which controllable solubilizes when contacted with water to provide a solution with sanitizing antimicrobial efficacy, said composition further comprising:
    (a) from about 5 wt-% to 60 wt-% of a sanitizer;
    (b) from about 10 wt-% to 70 wt-% of a hardener comprising a nonionic surfactant; and
    (c) from about 5 wt-% to 50 wt-% of a plasticizer wherein said hardener controls the consistency of said caulk and the dissolution rate of said caulk when subjected to an aqueous flow and said caulk has penetrometer softness ranging from about 150 mm to 400 mm, said caulk solubilizing at a rate to provide a solution having at least about 120 parts per million sanitizer when contacted with water.

11. The composition of claim 10 wherein said sanitizer is selected from the group consisting of an aldehyde compound, an iodophore complex, a carboxylic acid, a quaternary ammonium salt, a peracid compound, an interhalogen, a phenolic compound, a surface active agent, a halogen releasing agent and mixtures thereof.

12. The composition of claim 10 wherein said hardener additionally comprises a constituent selected from the group consisting of an amide compound, a nonionic surfactant, a starch compound, an inorganic salt, and mixtures thereof.

13. The composition of claim 10 wherein said caulk has a penetrometer softness ranging from about 250 mm to 400 mm.

14. The composition of claim 10 wherein said plasticizer comprises water, an alkyl alcohol, an aldehyde compound, a carboxylic acid, a polyol, an alkoxylated amine compound, a phosphate ester, a petroleum based hydrocarbon, a vegetable oil, and mixtures thereof.

15. An erodible sanitizing caulk composition which controllably solubilizes when contacted with water to provide a solution with sanitizing antimicrobial efficacy, said composition further comprising:

(a) from about 5 wt-% to 60 wt-% of a sanitizer;

(b) from about 10 wt-% to 70 wt-% of a hardener comprising a nonionic surfactant wherein said nonionic surfactant comprises a bis(alkyl alcohol ethoxylate) adipate having from about 20 to 60 moles of ethoxylation; and (c) from about 5 wt-% to 50 wt-% of a plasticizer wherein said hardener controls the consistency of said caulk and the dissolution rate of the caulk when subjected to an aqueous flow and said caulk has penetrometer softness ranging from about 150 mm to 400 mm, said caulk solubilizing at a rate to provide a solution having at least about 120 parts per million sanitizer when contacted with water.

16. The composition of claim 10 wherein said sanitizer comprises an acid anionic surfactant selected from the group consisting of dodecyl benzene sulfonic acid, sodium lauryl sulfate, sodium 1-octane sulfonate, and mixtures thereof.

17. An erodible sanitizing caulk composition which controllably solubilizes when contacted with water to provide a solution with sanitizing antimicrobial efficacy comprising from about 5 wt-% to 60 wt-% of an acid anionic surfactant sanitizer, and from bout 10 wt-% to 70 wt-% of a bis(alkyl alcohol ethoxylate) adipate having from about 20 to 60 moles of ethoxylation, said caulk having a penetrometer softness ranging from about 150 mm to 400 mm, said caulk solubilizing at a rate to provide a solution having at least about 120 parts per million sanitizer when contacted with water.

18. An erodible sanitizing caulk composition which controllably solubilizes when contacted with water to provide a solution with sanitizing antimicrobial efficacy comprising:

(a) from about 5 wt-% to 60 wt-% of a sanitizer, said sanitizer selected from the group consisting of an aldehyde compound, an iodophor complex, a carboxylic acid, a quaternary ammonium salt, a peracid compound, a peroxygen compound, an interhalogen, a phenolic compound, a halogen releasing agent, a surfactant, and mixtures thereof;

(b) from about 10 wt-% to 70 wt-% of a hardener, said hardener selected from the group consisting of an amide compound, a starch compound, an inorganic salt, and mixtures thereof wherein said hardener controls the consistency of said caulk and the dissolution rate of the caulk once subjected to an aqueous flow said caulk has a penetrometer softness ranging from about 150 mm to 400 mm, said caulk solubilizing at a rate adequate to provide a solution having at least about 120 parts per million sanitizer when contacted with water.

19. The composition of claim 18 additionally comprising from about 5 wt-% to 50 wt-% of a plasticizer.

20. The composition of claim 19 wherein said plasticizer is selected from the group consisting of water, an alkyl alcohol, an alkoxylated aldehyde compound, a carboxylic acid, a polyol, an amine compound, a phosphate ester, a petroleum based hydrocarbon, a vegetable oil, and mixtures thereof.

21. The composition of claim 18 wherein said sanitizer comprises an acid anionic surfactant selected from the group consisting of dodecyl benzene sulfonic acid, sodium lauryl sulfate, sodium 1-octane sulfonate, and mixtures thereof.

22. The composition of claim 18 wherein when subjected to an aqueous flow of about 70° F. or greater said caulk dissolves at a rate of about 5 wt-% or greater every five minutes.

23. The composition of claim 18 wherein said caulk has a penetrometer softness ranging from about 250 mm to 400 mm.

24. The composition of claims 1, 10, 15, 17 or 18 wherein said sanitizer comprises a quaternary ammonium compound selected from the group consisting of n-alkyl ($C_{12-18}$) dimethyl benzyl ammonium chloride, n-alkyl ($C_{14-18}$) dimethyl benzyl ammonium chloride, n-alkyl ($C_{12-14}$) ethyl benzyl ammonium chloride, n-alkyl ($C_{12-18}$) ethyl benzyl ammonium chloride, n-tetradecyl dimethyl benzyl ammonium chloride monohydrate, n-alkyl ($C_{12-14}$) dimethyl 1-naphthyl-methyl ammonium chloride and dodecyl dimethyl ammonium chloride, and mixtures thereof.

* * * * *